(12) United States Patent
Zamora

(10) Patent No.: US 7,468,210 B1
(45) Date of Patent: Dec. 23, 2008

(54) CROSS-LINKED HEPARIN COATINGS AND METHODS

(75) Inventor: Paul O. Zamora, Gaithersburg, MD (US)

(73) Assignee: BioSurface Engineering Technologies, Inc., Rockville, MD (US)

( * ) Notice: Subject to any disclaimer, the term of this patent is extended or adjusted under 35 U.S.C. 154(b) by 662 days.

(21) Appl. No.: 10/733,208

(22) Filed: Dec. 10, 2003

Related U.S. Application Data

(60) Provisional application No. 60/432,504, filed on Dec. 10, 2002.

(51) Int. Cl.
- *B05D 3/00* (2006.01)
- *A61K 31/727* (2006.01)
- *A61L 15/28* (2006.01)
- *C08B 37/10* (2006.01)

(52) U.S. Cl. .................. 428/447; 427/448; 427/2.1; 424/423; 424/447; 424/445; 514/56; 536/21

(58) Field of Classification Search .................. None
See application file for complete search history.

(56) References Cited

U.S. PATENT DOCUMENTS

| | | | | |
|---|---|---|---|---|
| 3,272,204 | A | 9/1966 | Artandi et al. | 128/334 |
| 4,193,138 | A | 3/1980 | Okita | 3/1.4 |
| 4,747,848 | A | 5/1988 | Maini | 623/1 |
| 4,842,575 | A | 6/1989 | Hoffman, Jr. et al. | 600/36 |
| 5,197,977 | A | 3/1993 | Hoffman, Jr. et al. | 623/1 |
| 5,509,899 | A | 4/1996 | Fan et al. | 604/96 |
| 5,510,418 | A | 4/1996 | Rhee et al. | 525/54.2 |
| 5,650,234 | A | 7/1997 | Dolence et al. | 428/447 |
| 5,665,114 | A | 9/1997 | Weadock et al. | 623/1 |
| 5,916,585 | A * | 6/1999 | Cook et al. | 424/426 |
| 5,945,457 | A | 8/1999 | Plate et al. | 514/772.1 |
| 5,955,588 | A * | 9/1999 | Tsang et al. | 536/21 |
| 6,051,648 | A | 4/2000 | Rhee et al. | 525/54.1 |
| 6,096,798 | A | 8/2000 | Luthra et al. | 523/105 |
| 6,099,562 | A | 8/2000 | Ding et al. | 623/1.46 |
| 6,120,904 | A | 9/2000 | Hostettler et al. | 428/423.3 |
| 6,231,600 | B1 | 5/2001 | Zhong | 623/1.42 |
| 6,231,892 | B1 | 5/2001 | Hubbell et al. | 424/491 |
| 6,248,057 | B1 | 6/2001 | Mavity et al. | 600/3 |
| 6,258,371 | B1 | 7/2001 | Koulik et al. | 424/422 |
| 6,270,788 | B1 | 8/2001 | Koulik et al. | 424/423 |
| 6,306,165 | B1 | 10/2001 | Patnaik et al. | 623/1.43 |
| 6,309,660 | B1 | 10/2001 | Hsu et al. | 424/425 |
| 6,342,591 | B1 | 1/2002 | Zamora et al. | 536/21 |
| 6,368,347 | B1 | 4/2002 | Maini et al. | 623/1.46 |
| 6,387,978 | B2 | 5/2002 | Ronan et al. | 523/113 |
| 6,406,687 | B1 | 6/2002 | Luthra et al. | 424/78.37 |
| 6,410,044 | B1 | 6/2002 | Chudzik et al. | 424/423 |
| 6,458,889 | B1 | 10/2002 | Trollsas et al. | 525/54.1 |
| 6,491,965 | B1 | 12/2002 | Berry et al. | 427/2.1 |
| 6,497,729 | B1 * | 12/2002 | Moussy et al. | 623/23.57 |
| 6,514,534 | B1 * | 2/2003 | Sawhney | 424/486 |
| 6,534,591 | B2 | 3/2003 | Rhee et al. | 525/54.1 |
| 6,585,765 | B1 * | 7/2003 | Hossainy et al. | 623/1.45 |
| 6,596,699 | B2 * | 7/2003 | Zamora et al. | 514/44 |
| 6,630,580 | B2 | 10/2003 | Tsang et al. | 536/21 |
| 6,818,018 | B1 * | 11/2004 | Sawhney | 623/11.11 |
| 6,921,811 | B2 * | 7/2005 | Zamora et al. | 536/21 |
| 6,984,393 | B2 * | 1/2006 | Amsden | 424/423 |
| 7,025,990 | B2 * | 4/2006 | Sawhney | 424/486 |
| 7,241,736 | B2 * | 7/2007 | Hunter et al. | 514/2 |
| 2002/0115836 | A1 | 8/2002 | Tsang et al. | 536/21 |
| 2002/0160098 | A1 | 10/2002 | Zamora et al. | 427/2.11 |

OTHER PUBLICATIONS

Zamora, Paul O.; Tsang, Ray; Pena, Louis A.; Osaki, Shigemasa; and Som, Prantika, "Local Delivery of Basic Fibroblast Growth Factor (bFGF) Using Adsorbed Silyl-heparin, Benzyl-bis (dimethylsilylmethyl)oxycarbamoyl-heparin," Bioconjugate Chem. 2002, 13, 920-926.

James Laredo, M.D., Ph.D., Lian Xue, M.D., Ph.D., Vicki A. Husak, Joan Ellinger, Howeard P. Greisler, M.D., "Silyl-heparin adsorption improves the in vivo thromboresistance of carbon-coated polytetrafluoropethylene vascular grafts," The America Journal of Surgery 186 (2003) 556-560.

* cited by examiner

*Primary Examiner*—Brian-Yong S Kwon
(74) *Attorney, Agent, or Firm*—Janeen Vilven; Stephen A. Slusher; Peacock Myers, P.C.

(57) ABSTRACT

A thromboresistant coating for a medical device, method of coating and coated medical device, the coating including an in situ cross-linked co-polymer of a cross-linkable biomolecule, preferably an adsorbable biomolecule such as a heparin activity biomolecule with at least one prosthetic hydrophobic unit, and a multifunctional crosslinking agent, such as a bis-variant of polyethylene glycol, polyethylene oxide, or polyethylene glycol, wherein the crosslinking is by means of covalent complexation through at least two functional groups of the multifunctional crosslinking agent.

21 Claims, 3 Drawing Sheets

CROSS-LINKED HEPARIN COATINGS AND METHODS

This application claims the benefit of the filing of U.S. Provisional patent Application Ser. No. 60/432,504, entitled "Cross-Linked Heparin Coatings and Methods", filed on Dec. 10, 2002, and the specification thereof is incorporated herein by reference.

BACKGROUND OF THE INVENTION

1. Field of the Invention (Technical Field)

The present invention relates to methods of making covalently cross-linked coatings for medical devices, and particularly cross-linked complex carbohydrate molecules such as heparin and related molecules, coatings made by such methods and medical devices including such coatings, particularly coated vascular graft devices.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Vascular Prosthetic Devices. Vascular prostheses made of knitted or woven fabric of a polyester (e.g. DACRON® polyester, a trademark of E.I. du Pont de Nemours & Co., Inc.) or of sheets of polytetrafluoroethylene (commonly known under the TEFLON® trademark) are currently available or have been described in the art. Expanded polytetrafluoroethylene (ePTFE) tubes have a microporous structure consisting of small nodes interconnected with many tiny fibrila. ePTFE is extruded into tubes to make vascular grafts. Although vascular grafts constructed using such material are generally clinically successful, there is a tendency for small bore vascular grafts to undergo thrombosis.

Several approaches have introduced polymers or coatings intended to minimize leaking around suture holes of the vascular prosthesis. U.S. Pat. No. 4,193,138 to Okita discloses introducing a water-soluble polymer into the pores of ePTFE material and then treating the polymer to render it water-insoluble. U.S. Pat. No. 5,665,114 to Weadock et al. disclosed filling the pores with solid biocompatible material of natural origin. A water-soluble substance is then introduced into the pores and treated to render it water-insoluble. For grafts made with knitted or woven fabrics, materials such as collagen or gelatin have been applied to the highly porous surface of such textiles. See, for example, U.S. Pat. Nos. 3,272,204; 4,747,848; 4,842,575 and 5,197,977. The materials are generally claimed to penetrate into the voids produced by the woven or knitted structure of the fabric and thus reduce blood leakage throughout the entire fabric, as well as at locations where sutures pass through the fabric. U.S. Pat. No. 6,368,347 to Maini et al. describes a layer of resilient, bioresorbable material on at least one wall where the material is substantially excluded from pores in the wall of the vascular prosthesis.

Heparin Coatings. A number of strategies have been described for complexing heparin to a surface for the purpose of rendering the surface thromboresistant. These methods include covalent conjugation of heparin directly to a substrate or alternatively adsorption of heparin onto a substrate. One example of an adsorbed heparin is U.S. Pat. No. 5,955,588 to Tsang et al., which describes a non-thrombogenic coating composition including a covalent complex of from 1 to 30 hydrophobic silyl moieties conjugated to heparin, with the hydrophobic silyl moieties bound to a surface via hydrophobic bonding interactions. A particular disadvantage of adsorbable heparins is that they generally have a short resident time in vivo and are easily leached over a period of hours. A number of direct conjugation procedures have been described in which heparin is either conjugated directly to the surface or conjugated via a spacer. Such chemistries are technically challenging and expensive, with some medical devices are not amenable to the chemistry. Medical devices made of polytetrafluoroethylene are particularly difficult to adapt to direct heparin conjugation strategies. Adsorption strategies suffer from the fact that the adsorbed materials are not covalently conjugated and are frequently quickly desorbed from the surface.

U.S. Pat. No. 6,096,798 to Luthra et al. describes polymers having non-thrombogenic properties that are prepared by copolymerizing monomers of at least three classes selected from (a) monomers having sulphate groups, (b) monomers having sulphonate groups, (c) monomers having sulphamate groups, (d) monomers having polyoxyalkylene ether groups, and (e) monomers having zwitterionic groups. The polymers can additionally be provided with anti-thrombogenic properties by including an additional co-monomer having a pendant heparin (or hirudin, warfarin or hyaluronic acid) group. In this method the polymer is prepared in a complex multistep chemistry, and then after preparation applied to a surface where it chemically reacts and results in polymer adhesion to the surface.

U.S. Pat. No. 6,258,371 to Koulik et al. describes a complex method of coating a biocompatible medical article that involves synthesizing, in an organic solvent and apart from the medical device, a mixture including a first hydrophobic monomer such as hydrophobic methacrylate or hydrophobic acrylate monomers, a second functional monomer having pendant chemically reactive amine groups capable of forming covalent bonds with biologically active compounds, and a third hydrophillic monomer, the synthesis yielding a co-polymer solution. The polymeric surface of the medical device is coated with the co-polymer solution and a biomolecule is then coupled onto the coated surface through the ordered steps of: (a) admixing heparin with a periodate solution, (b) reacting the admixture and adding cyanoborohydride, (c) diluting the reacted admixture and (d) treating the coated co-polymeric surface with the diluted reacted admixture to render the resulting treated and coated polymeric surface amphiphobic. A similar coating strategy is described in Koulik et al., U.S. Pat. No. 6,270,788.

Other patents disclosing various heparin coatings include U.S. Pat. Nos. 5,945,457, 6,309,660, 6,406,687, 6,458,889, 6,491,965, and 6,534,591, among others.

Use of Polyethylene Glycols in Coatings. Methods have been described using polyethylene glycols as coatings, both where the polyethylene glycols are applied passively, as described in U.S. Pat. No. 5,509,899, and where the polyethylene glycols are "preactivated" and conjugated directly to the surface. In order to be used as conjugated coatings, the polyethylene glycols need to "activated" such that they can be employed for covalent bonding. The activations typically involve modification of one or both of the terminal groups, for example so that hydroxyl groups of polyethylene glycol (PEG) are "activated". This has been done by the use of a number of reactive functional groups including cyanurylate, tresylate, N-hydroxysuccinimide derived active esters, carbonates, imidazolyl formates, 4-dithiopyridines, isocyanates, and epoxides.

Methods to attach activated PEGs directly to the surface of medical devices are described in U.S. Pat. No. 5,650,234 to Dolence et al. and U.S. Pat. No. 6,099,562 to Ding and Helmus. U.S. Pat. No. 5,650,234 to Dolence et al. describes mixed carbonate analogs of PEG that smoothly react with amino groups in aminoglycans and protein- and amino-containing surfaces to form stable, hydrolysis-resistant carbamate linkages. In one embodiment applied to a stainless steel substrate, surfaces are treated with a glow-discharge plasma to etch the surface, re-treated with a glow-discharge plasma to introduce a polymeric siloxane, treated yet again with a glow-discharge plasma to introduce amines, conjugated with activated PEG in large molar excess to conjugate one (but not both) ends of the PEG, and then conjugate to aminoglycans via the remaining activated site on the PEG. This coating is durable, but the method is cumbersome and requires a large number of steps. U.S. Pat. No. 6,099,562 describes a layered coating for release of biologically active materials including heparin, where the coating includes a polymeric undercoat incorporating a biologically active material, with a topcoat formed of a discontinuous coating disposed over the entire outer surface of the undercoat, thereby forming covered and uncovered areas of the undercoat throughout the entire outer surface. The topcoat can then be modified with an ammonia plasma to introduce amines and conjugate PEG. In this method the use of multiple layers is cumbersome. Both U.S. Pat. No. 5,650,234 and U.S. Pat. No. 6,099,562 used glow-discharge methods which are limited to coating "line-of-sight" surfaces, and are not generally applicable to devices with complex geometries, such as tubes or matrices.

U.S. Pat. No. 5,510,418 describes a biocompatible, biologically inert conjugate including a chemically derivatized glycosaminoglycan conjugated to a synthetic hydrophilic polymer, which may include a polyethylene glycol. This method teaches the use of such complexes as three-dimensional matrices. Coatings of this invention are accomplished by dipping the device into a solution containing glycosaminoglycan and synthetic polymer while crosslinking is occurring and allowing the adherent viscous coating to dry as crosslinking is completed. The use of a viscous coating results in a thick coating and makes penetration of matrices difficult. Furthermore, coatings of tubes are prone to variations in thickness along the length of the tubes due to wicking during drying. The method does not teach a way of allowing the heparin to interact with the surface to prolong resident time either by covalent conjugation to the surface or by adsorption methods.

It can be seen that the foregoing methods do not provide a simple and durable heparin coating, preferably a cross-linked heparin coating, which can be applied by means of simple chemistry steps, and particularly applied to microporous structures such as vascular grafts made from ePTFE. Thus a simple method of making a cross-linked heparin or other biomolecule coating on a surface to provide a durable thromboresistant coating is needed.

BRIEF SUMMARY OF THE INVENTION

The invention provides a method of forming a cross-linked coating on a medical device, which method includes the steps of immersing the medical device in a first solution including an organic solvent and a multifunctional crosslinking agent, and immersing the medical device in a second solution including an organic solvent and a cross-linkable biomolecule. It is to be understood that in general either step may occur first. In the method, prior to immersing the medical device in the first solution or second solution as provided, the medical device can be immersed in a wetting solution. In a preferred embodiment, the first solution does not include water and the second solution includes from about 10 to 80 percent water by volume. In one embodiment of the method, immersion in the solution including the multifunctional crosslinking agent occurs prior to immersion in the solution including a cross-linkable biomolecule, and the method further includes the step of immersing the medical device in the first solution including an organic solvent and a multifunctional crosslinking agent subsequent to immersing the medical device in the second solution. The multifunctional crosslinking agent can include a bis-variant of polyethylene glycol, polyethylene oxide, or polyethylene glycol. The cross-linkable biomolecule can be a cross-linkable adsorbable biomolecule, including a cross-linkable adsorbable heparin activity biomolecule.

In another embodiment, the invention provides a method of forming a thromboresistant coating on a porous surface of a medical device, which method includes the ordered steps of:
(a) providing a medical device with a porous surface;
(b) wetting the porous surface by immersion in a wetting solution;
(c) immersing the porous surface in a first solution including a first organic solvent and a multifunctional crosslinking agent;
(d) immersing the porous surface in a second solution including a second organic solvent and a cross-linkable biomolecule; and
(e) immersing the porous surface in the first solution including the first organic solvent and the multifunctional crosslinking agent.

In the ordered method, the porous surface of the medical device can include expanded polytetrafluoroethylene. The wetting solution can include an organic solvent, such as acetone, isopropanol, acetonitrile, methanol, ethanol or a combination thereof. The multifunctional crosslinking agent can consist of a bis-variant of polyethylene glycol, polyethylene oxide, or polyethylene glycol. In one embodiment, the multifunctional crosslinking agent is bis-(benzotriazole carbonate) polyethylene glycol. Where the multifunctional crosslinking agent is a bis-variant of polyethylene glycol, polyethylene oxide, or polyethylene glycol, it is at a concentration between about 0.001 mg/mL and 500 mg/mL, more preferably between about 0.2 mg/mL and 10 mg/mL. The first organic solvent can be acetonitrile or acetone, and preferably the first solution does not include water. Thus in one embodiment the first solution does not include water and the second solution includes from about 10 to 80 percent water by volume. The cross-linkable biomolecule can be a cross-linkable adsorbable biomolecule, and in a preferred embodiment, a conjugate of at least one prosthetic hydrophobic unit and a heparin activity biomolecule. The conjugate of at least one prosthetic hydrophobic unit and a heparin activity biomolecule can have from 1 to about 30 hydrophobic silyl moieties conjugated to the heparin activity biomolecule. In this embodiment, the heparin activity molecule with from 1 to about 30 hydrophobic silyl moieties conjugated thereto is at a concentration in the second solution of from about 0.01% to about 10%, and more preferably from about 25% to about 1.5%. In a preferred embodiment, the conjugate of from 1 to 30 hydrophobic silyl moieties and the heparin activity biomolecule is benzyl-bis(dimethylsilylmethyl)$_x$-oxycarbamoyl-heparin. The second organic solvent can be the same as the first organic solvent. In a preferred embodiment, the second solution further includes from about 10 to 80 percent water by volume. In the method, immersing in each step can be for between about 5 minutes and two hours, preferably where immersing the porous surface in the first solution is in each step for between about 15 minutes and about one hour, and immersing the porous surface in the second solution is for between about 45 minutes and about 75 minutes.

The invention further provides a thromboresistant expanded polytetrafluoroethylene vascular graft including a tubular expanded polytetrafluoroethylene construct with an interior lumen and a cross-linked co-polymer coating on the surface of the interior lumen, the cross-linked co-polymer coating consisting essentially of a conjugate of at least one prosthetic hydrophobic unit and a heparin activity biomolecule cross-linked with a bis-variant of polyethylene glycol, polyethylene oxide, or polyethylene glycol. In this graft, the conjugate of at least one prosthetic hydrophobic unit and a heparin activity biomolecule can be from 1 to 30 hydrophobic silyl moieties conjugated to the heparin activity biomolecule. The bis-variant of polyethylene glycol, polyethylene oxide, or polyethylene glycol can be bis-(benzotriazole carbonate) polyethylene glycol.

The invention further provides a medical device with a thromboresistant blood-contacting surface including at least one porous blood-contacting surface and a cross-linked co-polymer coating on the porous surface, the cross-linked co-polymer coating consisting essentially of a conjugate of at least one prosthetic hydrophobic unit and a heparin activity biomolecule cross-linked with a bis-variant of polyethylene glycol, polyethylene oxide, or polyethylene glycol. In this medical device, the at least one porous blood-contacting surface can include expanded polytetrafluoroethylene, or alternatively can include a woven polymeric surface. In the medical device, the conjugate of at least one prosthetic hydrophobic unit and a heparin activity biomolecule can be from 1 to 30 hydrophobic silyl moieties conjugated to the heparin activity biomolecule. The bis-variant of polyethylene glycol, polyethylene oxide, or polyethylene glycol can be bis-(benzotriazole carbonate) polyethylene glycol.

In yet another embodiment, the invention provides a thromboresistant coating for a medical device, including an in situ cross-linked co-polymer consisting essentially of a conjugate of at least one prosthetic hydrophobic unit and a heparin activity biomolecule cross-linked with a bis-variant of polyethylene glycol, polyethylene oxide, or polyethylene glycol. Here too the conjugate of at least one prosthetic hydrophobic unit and a heparin activity biomolecule can be from 1 to 30 hydrophobic silyl moieties conjugated to the heparin activity biomolecule, and the bis-variant of polyethylene glycol, polyethylene oxide, or polyethylene glycol can be bis-(benzotriazole carbonate) polyethylene glycol.

A primary object of the present invention is to provide a coating composition for contacting surfaces of implantable medical devices, particularly porous medical devices such as ePTFE vascular grafts or sheets or woven materials, wherein the composition includes a cross-linked co-polymer including a biomolecule and a multifunctional crosslinking agent, which cross-linked co-polymer is preferably attached to the contacting surface by hydrophobic interaction.

A further object of the invention is to provide a coating composition and method wherein the attachment to a substrate can be varied, such that in one embodiment the invention provides a cross-linked silyl-heparin and multifunctional crosslinking agent wherein the number of silyl moieties per heparin molecule is varied, thereby varying the hydrophobicity of the resulting cross-linked co-polymer.

A further object is to provide a coating composition and method wherein the biomolecule is a heparin activity molecule, including heparin and heparin derivatives.

A further object is to provide a coating composition wherein the biomolecule is a crosslinkable bioactive molecule other than a heparin activity molecule, including serum albumin and collagen.

A further object of the present invention is to provide a cost effective and commercially feasible method for coating polymeric medical devices, including medical devices with a porous microstructure, with a coating including a thromboresistant bioactive molecule.

A further object of the present invention is to provide a cost effective and commercially feasible method for coating polymeric medical devices, including medical devices with a porous microstructure, with a thromboresistant coating including a cross-linked silyl-heparin composition.

A primary advantage of the present invention is that it provides for coating contacting surfaces of medical devices of complex geometries and surfaces with a durable and low-cost coating that promotes the desired biological or therapeutic effect.

Other objects, advantages and novel features, and further scope of applicability of the present invention will be set forth in part in the detailed description to follow, taken in conjunction with the accompanying drawing, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
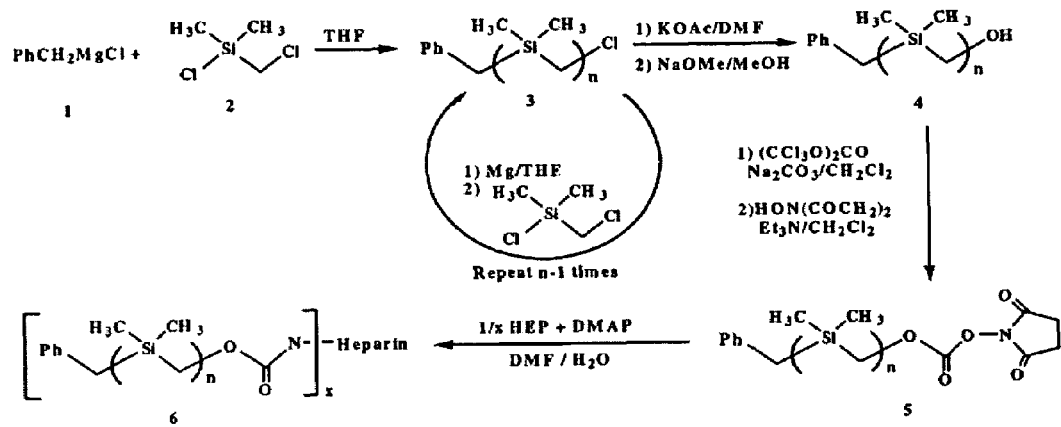
FIG. 1 is schematic of the synthesis of a silyated heparin employed in the invention.
Figure 2A:
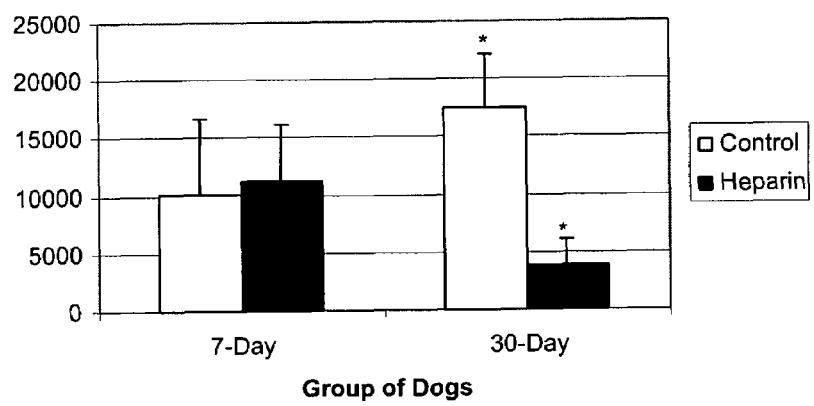
FIGS. 2A through 2D are graphs summarizing histologic parameters in dogs measured in grafts coated with cross-linked silyl-heparin of this invention and control grafts for both chronic 7-day and 30-day groups, where 2A shows graft thrombus length, with the Y axis depicting length of thrombus in microns, 2B shows average thrombus height, with the Y axis depicting average thrombus height in microns, 2D shows thrombus area, with the Y axis depicting thrombus area in square microns, and 2D shows the maximum height of graft thrombus, with the Y axis depicting height in microns, and where for 2A to 2D N=5, means are ±SD, and p value is determined by Student-T test.
Figure 2B:
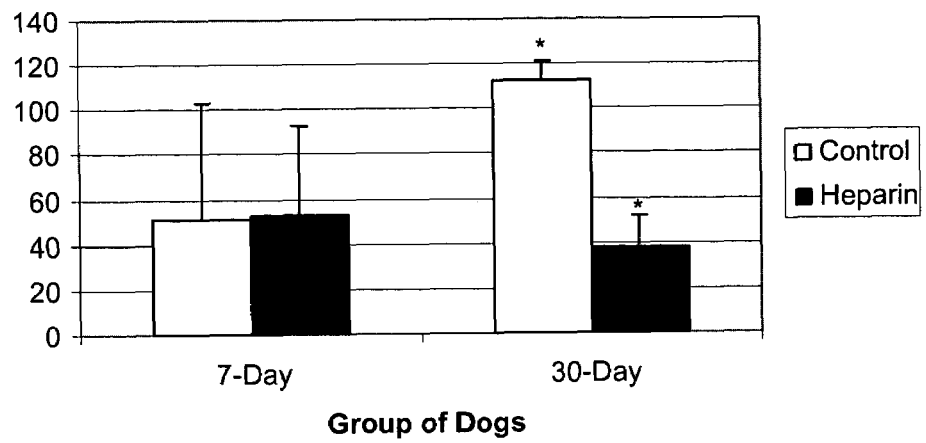
Figure 2C:
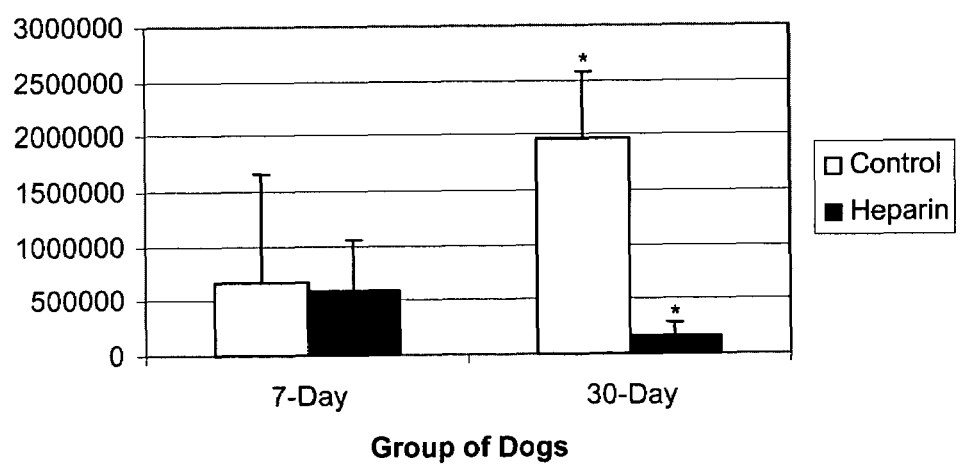
Figure 2D:
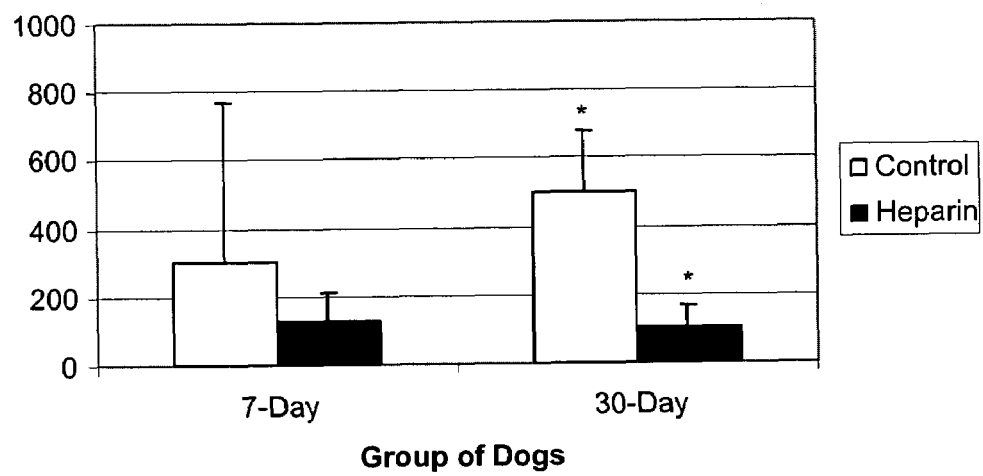

The present invention provides a method for making a biocompatible, thromboresistant medical device, and preferably a blood-compatible medical device, by means of a cross-linked co-polymer coating. The invention is composed of a cross-linkable biomolecule, preferably an adsorbable cross-linkable biomolecule, and a bifunctional crosslinking agent reacted such that the resulting co-polymer is formed in situ on a medical device. The resulting cross-linked co-polymer coating preferably has a resident time on the device longer, and preferably substantially longer, than that of either the biomolecule alone or the biomolecule adsorbed by conjugation of a prosthetic unit.

The invention provides a covalently cross-linked co-polymer coating, formed by the in situ crosslinking of a cross-linkable biomolecule, preferably a cross-linkable and adsorbable biomolecule, with a multifunctional crosslinking agent, wherein the crosslinking is through at least two functional groups of the multifunctional crosslinking agent. A preferred cross-linkable biomolecule is a heparin activity biomolecule, such as heparin and derivative and related molecules, including heparan sulfate, hyaluronic acid, dextran, dextran sulfate, chondroitin sulfate, dermatan sulfate, or a molecule including a mixture of variably sulfated polysaccharide chains composed of repeating units of D-glucosamine and either l-iduronic or D-glucuronic acids, salts of any of the foregoing and derivatives of any of the foregoing. Other biomolecules that may be used include chondroitin sulfate A, chondroitin sulfate C, dermatan sulfate, heparin, keratan sulfate, keratosulfate, chitin, chitosan 1, chitosan 2, and mixtures or derivatives of these glycosaminoglycans. An adsorbable biomolecule can include any biomolecule, including heparin activity biomolecules, which contain a hydrophobic prosthetic unit, such as benzylated silyl groups or alkane chains. In one embodiment silyl-heparin is an adsorbable biomolecule. Biomolecules may be employed which are not heparin activity biomolecules, providing that such biomolecules may be covalently cross-linked by means of the multifunctional crosslinking agent and are biologically active. The multifunctional crosslinking agent is a multifunctional compound with at least two functional groups, and includes bis-variants of polyethylene glycol, polyethylene oxide, and polyethylene glycol compounds as well as other carbon-based units including linear sequences and branched chains. In a preferred embodiment the multifunctional crosslinking agent is PEG with benzotriazole carbonate moieties as the active functional groups, but the multifunctional crosslinking agent may also include bis-variants of polyethylene glycol, polyethylene oxide, and polyethylene glycol compounds where the functional groups are homo- or hetero-functional groups such as succinimidyl esters, nitrophenyl activated esters, azidophenyl groups, maleimido groups, imido esters, carbodiimides, benzotriazole carbonates, epoxide groups, or aldehdye groups.

The covalently cross-linked co-polymer coating is preferably present on a porous structure, such as a structure including ePTFE. The coating is made, in part, by means of sequential deposition, such as by immersion in a solution, first of one member, such as the bioactive molecule, and second and separately by a second member, such as the multifunctional crosslinking agent. It is hypothesized, without wishing to be bound thereby, that particularly with porous structures the structure surface creates an interface boundary, such that for example a bioactive molecule in a suitable solvent enters the matrix of the porous structure and subsequently a multifunctional crosslinking agent is utilized in a second different suitable solvent, such that there is diffusion out of the bioactive molecule and diffusion in of the multifunctional crosslinking agent resulting in reaction of the two groups at an interface boundary proximate the surface of the porous structure.

The invention further provides a method for in situ crosslinking of a cross-linkable biomolecule, preferably a cross-linkable and adsorbable biomolecule, with a multifunctional crosslinking agent, wherein the crosslinking is by means of covalent complexation through at least two functional groups of the multifunctional crosslinking agent.

In one embodiment, the structure to be coated is made of ePTFE, such as a vascular graft structure. Because in part of the microstructure of the structure, including the porosity thereof, it is desirable to wet the structure. This may be done by means of a suitable wetting solvent, preferably a suitable organic solvent. In the case of ePTFE, one solvent that may be employed is acetone. Following wetting of the structure by immersion in a suitable solvent such as acetone for a period sufficient to result in wetting of the entire structure, the structure is transferred to a solution including either the biomolecule, preferably an adsorbable biomolecule, or the multifunctional crosslinking agent. The biomolecule or multifunctional crosslinking agent, as the case may be, is dissolved in a first solution preferably including an organic solvent. In one embodiment, the organic solvent employed to wet the structure is miscible, preferably completely miscible, with the organic solvent utilized for the biomolecule or multifunctional crosslinking agent. Following immersion of the structure in a solution including the biomolecule or multifunctional crosslinking agent, the structure is then immersed in a second solution containing the member not present in the first solution. The member in the second solution is similarly dissolved in a solution preferably including an organic solvent, and preferably an organic solvent that is miscible, preferably completely miscible, with the solvent of the first solution. In one embodiment, the same organic solvent is employed in both the first solution and the second solution, but in varying concentrations. Thus it may be seen that the first solution can include dissolved therein a biomolecule, preferably an adsorbable biomolecule, and the second solution can include dissolved therein a multifunctional crosslinking agent. Conversely, the first solution can include dissolved therein a multifunctional crosslinking agent and the second solution can include dissolved therein a biomolecule, preferably an adsorbable biomolecule. It is further possible and contemplated that one or more applications can be repeated, such that for example the following schemes may be employed: (a) immersion in first solution including the biomolecule, which is preferably an adsorbable biomolecule; (b) thereafter immersion in second solution including a multifunctional crosslinking agent; and (c) thereafter immersion in a third solution that is identical to first solution and includes a biomolecule and preferable an adsorbable biomolecule. Alternatively the following scheme may be employed: (a) immersion in a first solution including a multifunctional crosslinking agent; (b) thereafter immersion in a second solution including a biomolecule and preferable an adsorbable biomolecule; and (c) thereafter immersion in a third solution that is identical to the first solution and includes a multifunctional crosslinking agent. In the immediately preceding scheme, it is also possible and contemplated that the multifunctional crosslinking agent in the third solution can be different from the multifunctional crosslinking agent in the first solution, or alternatively it can be present in a different concentration. In instances where the first and third solution includes a biomolecule, the biomolecule may be different or alternatively present in different concentrations. For example, the first solution may include an adsorbable biomolecule, such as a silyl-heparin, while the third solution may include a biomolecule, such as heparin, that is less adsorbable than the adsorbable biomolecule. It may also be seen that either of the foregoing schemes can be extended to a fourth or subsequent solution. In any event, following immersion in the last solution including either a biomolecule or multifunctional crosslinking agent, the structure may be rinsed in an appropriate solvent, such as an organic solvent, to remove unreacted biomolecules or multifunctional crosslinking agents and any breakdown or other products resulting from the crosslinking reaction.

In a preferred embodiment, an adsorbable biomolecule is employed, wherein the biomolecule intrinsically contains reactive amino groups ($-NH_2$) for crosslinking, and further wherein one or more hydrophobic prosthetic units are conjugated to the biomolecule. Silyl-heparin is one example of an adsorbable biomolecule that may be so employed. In this embodiment, a preferred multifunctional crosslinking agent is a multifunctional compound with at least two functional groups, and includes bis-variants of polyethylene glycol, polyethylene oxide, and polyethylene glycol compounds as well as other carbon-based units including linear sequences and branched chains, and preferably PEG which contains benzotriazole carbonate moieties as the active functional groups. The method and coating is preferably employed with a substrate including matrices, such as an ePTFE structure.

For use with ePTFE structures, a preferred organic solvent for use as a wetting solution is acetone, with wetting by immersion of the ePTFE structure in acetone for a period between about ten minutes and one hour, preferably between about twenty minutes and forty minutes, at a temperature less than the boiling point of acetone, and preferably at a temperature between about 27° C. and 40° C., most preferably about 37° C. Other wetting agents may be employed, such as isopropanol, acetonitrile, methanol, ethanol and the like. Following wetting, the ePTFE structure is transferred to a first solution consisting of an organic solvent, such as 100% acetonitrile, and a multifunctional crosslinking agent, such as a bis-variant of polyethylene glycol, preferable bis-benzotriazole carbonate(polyethylene glycol) dissolved in acetonitrile at a concentration between about 0.001 mg/mL and 500 mg/mL, preferably between about 0.2 mg/mL and 10 mg/mL. Other solvents may be employed, such as for example acetone. In one embodiment a bis-benzotriazole carbonate (polyethylene glycol) with a molecular weight of between about 3,400 and 10,000 daltons is employed. Immersion is for a sufficient time to allow the multifunctional crosslinking agent to enter the ePTFE structure by means of diffusion, typically between about 5 minutes and 2 hours or more, preferably about 30 minutes, with immersion at any suitable temperature, such as room temperature. The ePTFE structure is removed from the first solution and immersed in a second solution consisting of a second organic solvent, such as 60% acetonitrile, and an adsorbable biomolecule, such as silyl-heparin, preferably a benzyl-bis(dimethylsilylmethyl)$_x$-oxycarbamoyl-heparin, at a concentration between about 0.01% and 10%, preferably between about 0.25% and 1.5%. Immersion is for a sufficient time to allow the adsorbable biomolecule to enter the ePTFE structure, adsorb to the structure thereof and cross-link with the multifunctional crosslinking agent, typically between about 5 minutes and 2 hours or more, preferably about one hour, with immersion at any suitable temperature, such as room temperature. In a preferred embodiment, the ePTFE structure is then immersed in a solution containing the multifunctional crosslinking agent, such as the first solution, for a suitable period of time, such as about 30 minutes. Alternatively, the order of immersion may be reversed, with the first solution including the adsorbable biomolecule such as a benzyl-bis(dimethylsilylmethyl)$_x$-oxycarbamoyl-heparin in 60% acetonitrile but with immersion preferable for about 30 minutes, and the second solution including the multifunctional crosslinking agent such as bis-benzotriazole carbonate(polyethylene glycol) in 100% acetonitrile but with immersion preferable for about one hour. In either instance, a third or subsequent application of an alternating substance may be made. Following the final immersion, the ePTFE structure may be rinsed, such as by rinsing in four serial changes of acetonitrile using a 15 minute incubation at each rinse.

It may be seen that while the foregoing uses the term "immersion", any of a variety of application methods may be employed and are contemplated thereby. For example, if the objective is to coat the interior lumen of a structure such as a tube, immersion may be by pumping or otherwise passing the various solutions through the tubing.

As used herein a "medical device" is defined as any article or device that has surfaces that contact tissue, blood, or other bodily fluids in the course of their operation. This includes, for example, extracorporeal devices for use in surgery such as blood oxygenators, blood pumps, blood sensors, tubing used to carry blood and other devices which contact blood which is then returned to the patient. This also includes endoprostheses implanted in blood contact in a human or animal body such as vascular grafts, stents, pacemaker leads, heart valves, and other devices implanted in blood vessels or in the heart. This also includes devices for temporary intravascular use such as catheters, guide wires, and other devices placed into blood vessels or the heart for purposes such as of monitoring or repair. Of particular utility in the practice of the invention are vascular grafts composed of extended polytetrafluoroethylene (ePTFE).

The medical device surfaces that may be coated by the present process include homo- and co-polymers, for example polyolefins, such as polyethylene, polypropylene, polyisobutylene, polybutadiene, polyisoprene, naturally occurring rubbers and polyethylene-copropylene; halogen-containing polymers, such as polyvinyl chloride, polyvinylidene chloride, polychloroprene, polytetrafluorothylene and polyvinylidene fluoride; polymers and co-polymers of vinylaromatic monomers, such as polystyrene, polyvinyltoluene, polystyrene-co-vinyltoluene, polystyrene-co-acrylonitrile and polystyrene-co-butadiene-co-acrylonitrile, polycondensates, for example polyesters, such as polyethylene terephthalate and polybutylene terephthalate; polyamides, such as polycaprolactam, polylaurolactam and the polycondensate of adipic acid and hexamethylenediamine; and polyurethanes, polyethers, polycarbonates, polysulfones, polyether ketones, polyester-amides and -imides, polyacrylonitrile, polyacrylates and polymethacrylates. Blends of two or more polymers or co-polymers can be used in medical device surfaces, as can combinations of various plastics that are joined to one another, such as by adhesive bonding, welding or fusion.

In a preferred embodiment, the medical device is an artificial vascular prosthesis used as a vascular graft, made from a porous material. One such material is ePTFE having a microstructure consisting of nodes interconnected by fibrils, such as fibrils from about 5 μm length up to about 100 μm length, and typically with fibrils from between about 20 and 40 μm length. In another preferred embodiment, the medical device is made from a porous material, such as a matrixed polymeric material. In yet another preferred embodiment, the porous material is a woven material.

A "multifunctional crosslinking agent" is a multifunctional compound with at least two functional groups, constituting a bifunctional crosslinking agent if two functional groups are present, such as bis-variants of polyethylene glycol, polyethylene oxide, and polyethylene glycol compounds as well as other carbon-based units including linear sequences and branched chains. The molecular weight of the multifunctional crosslinking agent is preferably between 3,000 and 11,000 daltons, but may be between 100 daltons and 500,000 daltons. The multifunctional crosslinking agent preferably contains benzotriazole carbonate as the active functional group, but may alternatively include functional groups selected from any of a number of agents known to those skilled in the art, and in particular bis-variants of polyethylene glycol, polyethylene oxide, and polyethylene glycol compounds where the functional groups are composed of homo- or hetero-functional groups such as succinimidyl esters, nitrophenyl activated esters, azidophenyl groups, maleimido groups, imido esters, carbodiimides, benzotriazole carbonates, epoxide groups, or aldehdye groups. A number of these compounds are commercially available. Of particular utility are bis(benzotriazole)polyethylene glycol and succinimidyl esters of polyethylene glycol such as bis(succininymidyl propionate) polyethylene glycol and bis(succininymidyl butanoate) polyethylene glycol. Other crosslinking agents such as bis[2-(succinimidyloxycarbonyloxy)-ethyl] sulfone, bis(sulfosuccinimidyl)suberate, 1,5 difluoro-2,4-dinitrobenzene, dimethyl adipimidate, dimethyl pimelimidate, dimethyl suberimidate, disuccinimidyl glutarate, dithiobis(succinimidyl proprionate), disuccinimidyl suberate, ethylene glycol bis(succinimidylsuccinate) and others known to those skilled in the art may similarly be employed.

An "organic solvent" is a solvent containing at least one component including carbon atoms, such as acetone, acetonitrile, methylene chloride, dimethyl formamide, tetrahydrafuran, methanol, ethanol, isopropanol, dimethyl sulfoxide, or the like or mixtures or combinations thereof. An organic solvent may include any percentage of water, such as a 60% organic solvent solution which includes 40% water.

An "adsorbable biomolecule" is a biomolecule that adheres to the surface of a medical device by hydrophobic interaction, particularly where the biomolecule has been rendered adsorbable by conjugation with one or more hydrophobic prosthetic units. Prosthetic units containing benzylated silyl groups or alkane chains are of particular utility. One adsorbable biomolecule is silyl-heparin as described in U.S. Pat. No. 5,955,588 and other silyl-heparin variants. Another adsorbable biomolecule is dodecyldimethylsilylmethyl heparin carbonate. The adsorbable biomolecule may also be inherently adsorbable.

A "biomolecule" is a cross-linkable biologically active molecule. A biomolecule may, but need not, constitute an adsorbable biomolecule. One such biomolecule is heparin. Heparin inhibits the coagulation of blood by interacting with antithrombin III and thrombin to inhibit the conversion of fibrinogen to fibrin. Other biomolecules include extracellular matrix molecules such as collagen, gelatin, elastin, fibronectin, glycosaminoglycans, antibacterial and antimicrobial agents; anticoagulant and antithrombotic agents; platelet agents; anti-inflammatories; enzymes; catalysts; hormones; growth factors; drugs; vitamins; antibodies; antigens; nucleic acids; dyes (which act as biological ligands); DNA and RNA segments; and proteins and peptides. The biomolecules can be synthetically derived or naturally occurring. Biomolecules also include heparin, heparin fragments, heparin-mimetics, prostaglandin $E_1$ (PGE$_1$), ticlopidine, plasmin, urokinase, tissue plasminogen activator, hirudin, dextran sulfates, gelatin, albumin, and bioactive polypeptides. Ticlopidine and prostaglandin $E_1$ inhibit the activation of platelets. Plasmin, urokinase, and TPA are serine proteases that lyse fibrin. Certain biomolecules contain reactive groups, such as amino groups ($-NH_2$) present in heparin, which may be employed in crosslinking. It is to be understood that the reactive group on the biomolecule must be complementary to the active functional group of the multifunctional crosslinking agent, such that on crosslinking a covalent bond linkage is formed. For biomolecules not containing an appropriate reactive group, a reactive group may be introduced by means of chemical modification.

A "heparin activity biomolecule" is a biomolecule which includes heparin or derivative and related molecules, including heparan sulfate, hyaluronic acid, dextran, dextran sulfate, chondroitin sulfate, dermatan sulfate, or any molecule including a mixture of variably sulfated polysaccharide chains composed of repeating units of D-glucosamine and either l-iduronic or D-glucuronic acids, salts of any of the foregoing, derivatives of any of the foregoing and combinations of any of the foregoing. A heparin activity molecule may be an adsorbable biomolecule, and specifically an adsorbable heparin activity biomolecule, when it includes one or more hydrophobic prosthetic units.

A "biocompatible" material is one that does not generally cause significant adverse reactions, such as toxic or antigenic responses in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction or rejection or inflammatory reaction.

A "blood compatible" material is one that will not induce undesirable reactions in the body as a result of contact with blood, such as blood clotting. This can be demonstrated by reduced thrombin generation, for example.

As used herein, "silyl-heparin" is a family of adsorbent molecules based on benzyl-bis(dimethylsilylmethyl)$_x$-oxycarbamoyl-heparin, and which may be synthesized in accord with procedures described generally in U.S. Pat. No. 5,955,588. Silyl-heparin is amphipathic and is readily adsorbed onto hydrophobic surfaces. Silyl-heparins are generally applied to surfaces such as medical devices by "dip-coating", such as application by immersion. Silyl-heparins are easy and simple to apply as a coating. They require no special equipment and no special technical skills for use, and can be applied to most metals and synthetic polymers used in the construction of medical devices including polypropylene, polyethylene, polyurethane, polyvinyl chloride, poly tetrafluoroetheylene, polycaprolactone, and poly (lactide:coglycolide), as well as stainless steel, titanium, and platinum.

In one embodiment, the medical device is a vascular graft. The vascular graft may be composed entirely or in part of ePTFE, DACRON® synthetic fibers, polyurethane, or other appropriate materials. Preferably, the vascular graft has a porous microstructure.

Preferably, a porous medical device such as a vascular graft is wetted by treatment with an organic solvent. The need for the use of a wetting agent is determined by the chemical nature and geometry of the medical device, and may, in some cases, not be required or desired.

The medical device is treated with a multifunctional crosslinking agent dissolved in an organic solvent such as acetonitrile. Ideally, the wetting agent, if used, should be completely miscible with the organic solvent employed with the multifunctional crosslinking agent.

The multifunctional crosslinking agent preferably includes a PEG. The functional groups of the multifunctional crosslinking agent are preferably composed of benzotriazole carbonate or succinimidyl groups. In one embodiment the molecular weight of the multifunctional crosslinking agent is preferably approximately 3,800 daltons.

In one embodiment, bis-benzotriazole carbonate(polyethylene glycol) (BTC-PEG) is dissolved in acetonitrile and the medical device immersed in the solution. The concentration of BTC-PEG can range from 0.001 mg/mL to 500 mg/mL, but preferably is between about 0.2 and 10 mg/mL. The length of time the medical device is immersed can range from about 5 minutes to 2 hours or more but is preferably about 30 minutes. In the case of a porous device such as a porous vascular graft, the BTC-PEG enters the wall of the vascular graft by diffusion.

The BTC-PEG-treated medical device is transferred to a solution, miscible with the BTC-PEG solution, which contains the adsorbable biomolecule. In one embodiment, the adsorbable biomolecule is a silyl-heparin dissolved in 60% acetonitrile. As the BTC-PEG diffuses out from the porous medical device such as a porous vascular graft and the silyl-heparin diffuses in and is adsorbed to the medical device surface, the functional groups of the BTC-PEG react with the silyl-heparin thereby resulting in an adsorbed, cross-linked co-polymer coating that is thromboresistant. Synthesis of the coating is carried out using a proportion of multifunctional crosslinking agent and adsorbable biomolecule to optimize the polymerization of the biomolecule, bioactivity, and removal of unreacted multifunctional crosslinking agent or its hydrolysis products. This allows for a simultaneous in situ polymerization of the biomolecule and coating of the medical device.

Unreacted BTC-PEG and breakdown products are removed by repeated rinsing in an appropriate solvent, typically acetonitrile. Acetonitrile is of particular utility when used with vascular grafts composed of ePTFE, as drying from this solvent does not result in shrinkage or foreshortening of the graft. Thereafter, the vascular graft is air-dried at a suitable temperature, such as 56° C., although any number of drying conditions may be used.

The present invention provides a simple method for making a biocompatible, thromboresistant medical device, and preferably, a blood compatible medical device, through the use of a cross-linked co-polymer coating. The invention is composed of an adsorbable biomolecule and a multifunctional crosslinking agent reacted such that the resulting co-polymer is deposited in situ on a medical device. The following generally describes methods applicable to vascular grafts composed of ePTFE utilizing a silyl-heparin adsorbable biomolecule. The vascular graft is wetted by immersion in acetone and then transferred to a solution containing acetonitrile and BTC-PEG. The BTC-PEG enters the pores of the graft by diffusion. The BTC-PEG impregnated graft is transferred to a solution containing silyl-heparin dissolved in 60% acetonitrile. As silyl-heparin has low solubility in 100% acetonitrile, it tends to accumulate at the interface of the acetonitrile diffusion gradient that is moving to the outside of the graft. This interface moves interior to the wall of the graft as the acetonitrile diffuses out providing the BTC-PEG crosslinking agent the highest probability of reacting with target groups, here amines, in the silyl-heparin. As the silyl-heparin is diffusing into the graft it is also adsorbed onto the surface of the graft by means of the silyl prosthetic groups. The overall result of the silyl-heparin adsorption onto the graft surface and crosslinking in situ is a network of cross-linked silyl-heparin-PEG. The network of silyl-heparin-PEG benefits from the multiplicity of adsorption sites on the polymer with a consequent increase in resident time on the graft surface. The multiplicity of adsorption sites contributes synergistically to the resident time of the heparin molecules on the surface.

The use of 60% acetonitrile as a solvent for silyl-heparin has additional advantages relative to BTC-PEG. Benzotriazole hydrolysis products and PEG are soluble in 60% acetonitrile, thereby reducing the concentration of such products in the graft wall. Benzotriazole hydrolysis products are also soluble in the acetonitrile used in the wash steps, thereby further reducing the concentration of breakdown products.

The resulting co-polymer coating has a resident time on the device longer than that of either the biomolecule alone or an adsorbable biomolecule alone, such as biomolecule conjugated to an adsorbable prosthetic unit.

The order of introducing the components of the invention is variable. For example, the multifunctional crosslinking agent can be applied first to the medical device and followed by an adsorbable biomolecule. Alternatively, the adsorbable biomolecule can be applied first and followed by the multifunctional crosslinking agent. In yet another embodiment, the multifunctional crosslinking agent is applied first to the medical device, followed by an adsorbable biomolecule, and then followed by application with a multifunctional crosslinking agent. In the latter case the initial and subsequent multifunctional crosslinking agents may be the same or different, and may be at the same or different concentrations.

It has surprisingly been found that the residence time of the covalently cross-linked co-polymer coating, such as in vivo residence time after coating on a vascular graft composed of ePTFE, is longest when the multifunctional crosslinking agent is applied first, followed by application of the adsorbable biomolecule in an organic solvent including water, and then followed by a second application of the multifunctional crosslinking agent. For example, when the multifunctional crosslinking agent is BTC-PEG, and the adsorbable biomolecule is silyl-heparin, residence time is longer using this method than is the case where silyl-heparin is applied first, followed by BTC-PEG, and then followed by a second application of silyl-heparin. Thus while either order may be followed, in a preferred embodiment the multifunctional crosslinking agent, such as BTC-PEG, is applied first.

Experimental data further established that with medical devices such as a vascular graft composed of ePTFE, a coating formed by immersion of the medical device in a solution consisting of heparin came off or disassociated from the medical device very quickly, that a coating formed by immersion in a solution consisting of silyl-heparin came off or disassociated from the medical device less quickly, that a coating formed by sequential immersion in silyl-heparin followed by BTC-PEG came off or disassociated from the medical device still less quickly, and that a coating formed by sequential immersion in BTC-PEG followed by silyl-heparin came off or disassociated from the medical device the slowest of all coatings using a two-step immersion. The slowest disassociation rate was observed with a coating employing a three-step immersion, formed by sequential immersion in BTC-PEG followed by silyl-heparin and followed by BTC-PEG as a last immersion step. Thus in a preferred embodiment a three-step immersion is employed, utilizing a multifunctional crosslinking agent in the first step, an adsorbable biomolecule in the second step, and the multifunctional crosslinking agent in the third step.

In the case of heparin activity biomolecules, cross-linking with a multifunctional crosslinking agent such as BTC-PEG did not result in the desired residence time of the coating where the heparin did not contain one or more hydrophobic prosthetic units, such as a silyl moiety. Thus cross-linked silyl-heparin had a statistically relevant longer residence time than did cross-linked heparin.

The chemistry employed in the method of this invention advantageously may be simply and conveniently modified for specific applications. For example, the hydrophobicity of a heparin molecule may be varied by varying the number of silyl moieties per heparin molecule. The heparin load on a medical device may be varied by changing either the concentration of heparin or the incubation time, or both. For example, heparin concentrations, such as silyl-heparin concentrations, may vary from about 0.1% to about 1% or greater. Similarly, incubation time may vary from less than five minutes to two hours or more.

The method of this invention further provides a number of advantages over more complex chemistries. For example, many chemistries employ introduction of "tether" group to a substrate, such as introducing an amino group to a medical device surface. Sequential steps then add a thromboresistant component such as heparin, optionally followed by one or more crosslinking agents. However, any such coating including heparin will degrade over time, due to a variety of biological and mechanical factors. In the instance of introduced tether groups, a "nub" or part of the molecule is frequently left permanently attached to the medical device, which molecular structure may precipitate an antigenic, allergic or inflammatory reaction. By contrast, in the method of this invention the heparin is bound to the substrate by means of a hydrophobic prosthetic unit, such that the heparin molecule is adsorbable, and thus the entire heparin molecule is removed by biological or mechanical factors, without leaving a residual nub or part of the molecule.

In the prior art, at least one patent, U.S. Pat. No. 6,051,648, discloses mixing a first synthetic polymer and a second synthetic polymer, and applying a thin layer of the reaction mixture before substantial crosslinking has occurred between the nucleophilic groups on the first synthetic polymer and the electrophilic groups on the second synthetic polymer. However, this method has a number of substantial drawbacks. In the case of reagents such as silyl-heparin and BTC-PEG, if they are mixed in a solution crosslinking proceeds very quickly, with the cross-linked co-polymer precipitating out of solution. The rate of crosslinking is dependent on a variety of parameters, including temperature, concentration, pH, and the like, many of which are difficult to closely control. Additionally, the method does not permit sufficient deposition of cross-linked co-polymer in highly matrixed or porous materials, such as ePTFE.

It is frequently advantageous to have the solvent for the multifunctional crosslinking agent differ from the solvent for the adsorbable biomolecule for a number of reasons. If the solvents differ, such as a first solvent containing 100% organic solvent and a second solvent containing 60% of the same organic solvent and the balance water, there is an osmotic pressure difference between the first solvent and the second solvent. This is hypothesized to result in a solvent interface boundary, thereby facilitating crosslinking between the reagents. Additionally, with many multifunctional crosslinking agents the solvent can be selected such that crosslinking is enhanced. For example, the reactive groups on BTC-PEG are significantly more labile or reactive on exposure to water. Thus the BTC-PEG can be employed in a first solvent that is composed of 100% organic solvent, with silyl-heparin in a second solvent that includes 40% water. The water in the second solvent activates or increases the reactivity of the reactive groups on BTC-PEG, thereby increasing the rate and efficiency of crosslinking.

INDUSTRIAL APPLICABILITY

The invention is further illustrated by the following non-limiting examples.

EXAMPLE 1

FIG. 1 depicts a scheme for preparation of silyl-heparin. Treatment of benzylmagnesium chloride 1 with chloro(chloromethyl)-dimethylsilane 2 gave benzyl(chloromethyl)dimethysilane 3 (n=1). 3 then underwent a repetitive reaction resulting in chain elongation. For chain elongation, treatment of 3$n$ with magnesium gave the Grignard Reagent which was, in turn, treated with chloro-(chloromethyl)dimethylsilane 2 to give the homologous silyl compound 3 n+1. This Grignard reaction was repeated as needed to obtain the desired chain length for the silyl compound. At the desired chain length, 3 (or 3$n$) was treated with potassium acetate, followed by transesterification of the corresponding acetate with basified methanol to give the alcohol 4. The alcohol 4, when treated with triphosgene, gave the corresponding chloroformate, which on treatment with N-hydroxysuccinimide gave the N-hydroxysuccinimidyl carbonate 5. Heparin was conjugated to 5 in 1:1 DMF/$H_2O$, where DMF is dimethyl formamide, containing 4-(dimethylamino)pyridine to give the silylated heparin 6. Adjusting the molar ratios of the reactants controlled the number of prosthetic groups per heparin. The silyl-heparin employed ammonium ion-free heparin of an average molecular weight of 10,000, where n=3 and on average x=4. The reaction scheme and method is described in more detail in Zamora et al., *Bioconjugate Chem.* 13:920-926 (2002), and in U.S. Pat. No. 6,342,591, on which the inventor herein is a co-inventor, and both are incorporated herein by reference.

EXAMPLE 2

CARBOFLO® vascular graft material made of ePTFE with carbon impregnation of approximately 25-30% of the luminal wall by coextrusion (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate (polyethylene glycol) (molecular weight approximately 3.4 K daltons). The grafts were incubated in this solution for 30 minutes at room temperature. The grafts were then transferred to an aqueous solution containing 60% acetonitrile and 1.5% silyl-heparin of Example 1 and allowed to incubate for 1 hour at room temperature. The grafts were then rinsed in four serial changes of acetonitrile using a 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assays that colorimetrically detected the heparin-induced inhibition of factor Xa activity.

EXAMPLE 3

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were then transferred to an aqueous solution containing 60% acetonitrile and 1.5% silyl-heparin of Example 1 and allowed to incubate for 30 minutes at room temperature. The grafts were transferred to freshly prepared aqueous solution containing 60% acetonitrile and 0.34 mg/mL of bis-benzotriazole carbonate (polyethylene glycol) (molecular weight approximately 3.4 K daltons). The grafts were incubated in this solution for 1 hour at room temperature. The grafts were then rinsed in four serial changes of acetonitrile using 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 4

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate (polyethylene glycol) (molecular weight approximately 3.4 K daltons). The grafts were incubated in this solution for 30 minutes at room temperature. The grafts were then transferred to an aqueous solution containing 60% acetonitrile and 1.5% silyl-heparin of Example 1 and allowed to incubate for 1 hour at room temperature. The grafts were transferred to an acetonitrile solution containing 0.34 mg/mL of bis-benzotriazole carbonate (polyethylene glycol) (molecular weight approximately 3.4 K daltons). The grafts were incubated in this solution for 30 minutes at room temperature. The grafts were then rinsed in four serial changes of acetonitrile using 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 5

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate (polyethylene glycol) (molecular weight approximately 10 K daltons). The grafts were incubated in this solution for 30 minutes at room temperature. The grafts were then transferred to an aqueous solution containing 60% acetonitrile and 1.5% silyl-heparin of Example 1 and allowed to incubate for 1 hour at room temperature. The grafts were then rinsed in four serial changes of acetonitrile using 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 6

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-succinimidyl butanoate (polyethylene glycol) (SBA2-PEG; molecular weight approximately 3.4 K daltons). The grafts were incubated in this solution for 30 minutes at room temperature. The grafts were then transferred to an aqueous solution containing 60% acetonitrile and 1.5% silyl-heparin of Example 1 and allowed to incubate for 1 hour at room temperature. The grafts were then rinsed in four serial changes of acetonitrile using 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 7

Synthesis of Adsorbable Heparin Based on Conjugation of Dodecyl Groups

Grignard Reaction of Dodecyl magnesium bromide and Chloro(chloromethyl)-dimethylsilane.

Under a nitrogen atmosphere, $ClSiMe_2CH_2Cl$ was dissolved in tetrahydrofuran (THF) and then cooled in an ice/acetone bath. DodecylMgCl was then slowly introduced in a 1 M solution such that the temperature was maintained below 10° C. The reaction was allowed to proceed with stirring overnight, after which a white suspension was obtained. Saturated aqueous $NH_4Cl$ was added to quench the reaction. The reaction mixture was mixed with hexane and the mixture allowed to partition. The organic phase was removed by the addition of hexane and the 2 phases were shaken vigorously and partitioned. Residual water was removed from the organic phase with $MgSO_4$, and the reaction product dodecyldimethylsilylmethylchloride concentrated under vacuum.

Acetolysis of Dodecyldimethylsilylmethylchloride. Dodecyldimethylsilylmethylchloride was dissolved in dimethylformamide and KOAc was added followed addition of $nBu_4NI$. The suspension was heated to 120° C. and allowed to react to completion. The reaction mixture was cooled and quenched by adding an aliquot of a saturated aqueous NaCl solution. The reaction product was extracted by the addition of hexane and partitioning. Residual water was removed from the organic phase with $MgSO_4$, and the reaction product dodecyldimethylsilylmethyl acetate concentrated under vacuum.

Trans-esterification of Dodecyldimethylsilylmethyl acetate with Methanol. Dodecyldimethylsilylmethyl acetate was dissolved in methanol, freshly prepared NaOMe was added to adjust pH>10, and the reaction mixture heated to reflux. The reaction was allowed to proceed to completion, and then concentrated under vacuum. The reaction product was extracted by the addition of hexane and partitioning. Residual water was removed from the organic phase with $MgSO_4$, and the reaction product dodecyldimethylsilylmethyl alcohol concentrated under vacuum.

Conversion of Dodecyldimethylsilylmethyl alcohol to the chloroformate. Triphosgene was dissolved with stirring in $CH_2Cl_2$ at 10° C. under $N_2$. Subsequently, $Na_2CO_3$ was added, followed by the addition of dodecyldimethylsilylmethyl alcohol (in $CH_2Cl_2$) such that the temperature was maintained below 10° C. The reaction was allowed to proceed to completion. The reaction product, a precipitate, was collected and washed with $PhCH_3$.

Conversion of Dodecyldimethylsilylmethyl chloroformate to the N-hydroxy-succinimidyl carbonate. Dodecyldimethylsilylmethyl chloroformate was dissolved in $CH_2Cl_2$ and cooled in an ice/acetone bath to ~10° C. N-hydroxy-succinimide was added in a bolus with $Et_3N$ added dropwise to maintain the temperature below 20° C. An aliquot of saturated aqueous $NaHCO_3$ was added and the mixture allowed to partition. The organic phase contained the reaction product. Residual water was removed from the organic phase with $MgSO_4$, and the reaction product concentrated under vacuum. Residual water was removed from the organic phase with $MgSO_4$, and the reaction product dodecyldimethylsilylmethyl N-succinimidyl carbonate was concentrated under vacuum.

Conjugation of Heparin to give dodecyldimethylsilylmethyl heparin carbonate. Sodium heparin was dissolved in water to give a 20% solution. Aliquots of DMF and dimethyl aminopipiridine were added. Dodecyldimethylsilylmethyl N-succinimidyl carbonate dissolved in DMF was added dropwise over at least 2 hrs. The crude product was triturated and collected by filtration. Water was removed by evaporated in a vacuum desiccator. The ivory powder was purified by continuous extraction with acetone in a large soxhlet extractor for ~3 days.

Coating solution. The resulting silyl-heparin was dissolved in water. Acetonitrile was added slowly with mixing such that the final concentration of acetonitrile was 60% and the final concentration of silyl-heparin was 1.0%.

EXAMPLE 8

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate(polyethylene glycol) (molecular weight approximately 3.4 K daltons). The grafts were incubated in this solution for 30 minutes at room temperature. The grafts were then transferred to an aqueous solution containing 60% acetonitrile and 1.0% silyl-heparin of Example 7 and allowed to incubate for 1 hour at room temperature. The grafts were then rinsed in four serial changes of acetonitrile using a 15 minute incubation at each rinse. The grafts were then air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 9

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were then transferred to an aqueous solution containing 60% acetonitrile and 1.5% silyl-heparin of Example 1 and allowed to incubate for 30 minutes at room temperature. The grafts were transferred to freshly prepared solution of phosphate buffered saline containing 60% acetonitrile and 0.34 or 3.4 mg/mL of disuccinimidyl suberate. The grafts were incubated in this solution for 1 hour at room temperature. The grafts were rinsed in four serial changes of acetonitrile using a 15 minute incubation at each rinse. The grafts were air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 10

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.1 mg/mL of 2,2'(methylethylidene)-bis-4,1 (phenyleneoxymethylene)-bis-oxirane polymer with α-hydro-ω-hydropoly(oxy-1,2-ethanediyl)-bis-(2-hydroxytriazole) carbonate. The grafts were incubated in this solution for 30 minutes at room temperature. The grafts were transferred to an aqueous solution containing 60% acetonitrile and 1.5% silyl-heparin of Example 1 and allowed to incubate for 1 hour at room temperature. The grafts were rinsed in four serial changes of acetonitrile using 15 minute incubation at each rinse. The grafts were air-dried at 56° C. for at least 2 hours. The presence of heparin on the grafts was confirmed by staining with 0.01% aqueous dimethylmethylene blue and by use of a commercially available kit assay that colorimetrically detected the heparin-induced inhibition of factor Xa activity.

EXAMPLE 11

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate(polyethylene glycol) (molecular weight approximately 3.4 K daltons). The grafts were incubated in this solution for 30 minutes at room temperature. The grafts were then transferred to an aqueous solution pH 7.4 containing 60% acetonitrile and 1% bovine serum albumin and allowed to incubate for 1 hour at room temperature. The grafts were then rinsed in four serial changes of acetonitrile using 15 minute incubation at each rinse. The grafts were then air-dried at 56° C. for at least 2 hours. The presence of protein was detected by staining the grafts with 0.01% aqueous crystal violet.

EXAMPLE 12

CARBOFLO® vascular graft material (4 mm diameter) was cut to lengths of 8 cm. The grafts were immersed in acetone for 30 minutes at 37° C. until all air bubbles had disappeared and the graft "cleared" indicative of complete wetting. The grafts were transferred to an acetonitrile solution containing 0.34 mg/mL of bis-benzotriazole carbonate(polyethylene glycol) (molecular weight approximately 3.4 K daltons). The grafts were incubated in this solution for 30 minutes at room temperature. The grafts were then transferred to an aqueous solution pH 7.4 containing 60% acetonitrile and 0.3 mg/mL of collagen and allowed to incubate for 1 hour at room temperature. The grafts were transferred to an acetonitrile solution containing 0.34 mg/mL of bis-benzotriazole carbonate(polyethylene glycol) (molecular weight approximately 3.4 K daltons). The grafts were then rinsed in four serial changes of acetonitrile using a 15 minute incubation at each rinse. The grafts were then air-dried at 56° C. for at least 2 hours. The presence of collagen was detected by staining the grafts by immersion in 0.1% Sirius Red in saturated picric acid for 1 hour followed by acidification in dilute acetic acid (5 mL glacial acetic acid per liter of water).

EXAMPLE 13

Flow loop studies. CARBOFLO® vascular graft material was prepared as in Example 2 with the following changes:

"No crosslink" grafts were wetted by immersion in acetone and then transferred to a 60% acetonitrile aqueous solution containing 0.25% silyl-heparin of Example 1 without introduction or use of any multifunctional crosslinking agent.

"Crosslink 1", "Crosslink 2" and "Crosslink 3" grafts were wetted by immersion in acetone, and then transferred to an acetonitrile solution containing, respectively, 0.5 mg/mL bis-benzotriazole carbonate(polyethylene glycol) (molecular weight approximately 10 K daltons), 0.34 mg/mL bis-benzotriazole carbonate(polyethylene glycol) (molecular weight approximately 3.4 K daltons), or 3.4 mg/mL bis-benzotriazole carbonate(polyethylene glycol) (molecular weight approximately 3.4 K daltons), followed in each instance by incubation in a 60% acetonitrile aqueous solution containing 0.25% silyl-heparin of Example 1.

Peristaltic pump-driven flow loop systems were constructed and operated in a 37° C. incubator. Four-headed peristaltic pump units were used with each graft tested isolated on a dedicated flow loop. Silastic tubing was used for the primary feed lines. Each flow loop contained a total volume of 150 mL of phosphate buffered saline containing 5% bovine serum plus 0.05% sodium azide as a bacteriostatic agent (PBS-BSA). Flow was delivered from reservoirs containing 125 mL of PBS-BSA under pulsile flow at a flow rate of approximately 25 mL/minute through the lumen of the coated 8 cm long CARBOFLO® vascular grafts (diameter 4 mm). The grafts were held in a secondary reservoir (test tube with closure) each containing a total volume of approximately 25 mL of PBS-BSA such that the solution flowed through the lumen of the graft and exited at the top of the reservoir, thereby also flushing the outside of the graft. A catheter was placed in the exit tubing to allow the periodic collection of samples. Prior to introduction of the graft and PBS-BSA, the systems were flushed with sterile saline and then sterile phosphate buffered saline to lower bioburden.

At the end of 7 days the grafts were removed from the flow loops and the inner lumens tested for heparin using a commercially available kit that measures the inhibition of clotting time, with the results shown on Table 1 below.

TABLE 1

| SAMPLE | CLOTTING TIME IN MINUTES | HEPARIN CONCENTRATION IN mIU/cm$^2$ |
|---|---|---|
| No crosslink | 2.5 | 58 |
| Crosslink 1 | 4.167 | 99 |
| Crosslink 2 | >20 | >125 |
| Crosslink 3 | 13.067 | >125 |

EXAMPLE 14

CARBOFLO® vascular graft material was coated as in Example 2, with a test sample containing heparin without a conjugated silyl prosthetic unit. The residence time of the cross-linked PEG-heparin coating on the substrate was significantly less than the residence time of the cross-linked PEG-silyl-heparin coating, indicating that the presence of the hydrophobic silyl moiety on the heparin molecule significantly increased adsorption of the coating to the substrate.

EXAMPLE 15

Control grafts were carbon-coated, 4 mm internal diameter, 5 cm long ePTFE, 30 µm internodal distance, without outer support. Experimental grafts were control grafts that underwent cross-linked silyl-heparin bonding. Briefly, grafts were wetted by immersion in acetone and then transferred to a 100% acetonitrile solution containing 0.5 mg/mL of bis-(benzotriazole carbonate) polyethylene glycol (BTC-PEG) (Nektar Therapeutics, San Carlos, Calif.) for 30 minutes. The grafts were then immersed in 60% acetonitrile solution containing 1% silyl-heparin (benzyl-tetra (dimethylsilylmethyl) oxycarbamoyl-heparin) for 1 hour, following which the grafts were reimmersed in the BTC-PEG solution for 30 minutes. The grafts were rinsed in several changes of acetonitrile and air-dried at 56° C.

Adult mongrel dogs (19-26 kg) underwent standard preoperative evaluation which included platelet aggregometry, laboratory measurement of prothrombin time, activated partial thromboplastin, and complete blood count. All dogs displayed nonaggregator profiles and all laboratory measurements were consistent with normal controls. After an overnight fast, the dogs were anesthetized, intubated, and ventilated, following which exposure of the infrarenal aorta and iliac arteries was obtained through a midline incision. The infrarenal aorta, its branches, and iliac arteries were dissected and the median sacral artery was ligated and divided. Bilateral aorto-iliac grafting was then performed, where one experimental and one control graft was placed on either (alternating) side. Graft anastomoses were performed with continuous 6-0 polypropylene suture (on a BV-1 needle) in an end-to-side fashion proximally on the aorta and distally in an end-to-end fashion with the common iliac arteries. The transected proximal common iliac arteries were ligated. Unclamping and exposure to blood was identical for both experimental and control grafts.

Overall chronic graft patency (7-day and 30-day groups) was 100% for the cross-linked silyl-heparin (16/16) grafts versus 68.75% for control (11/16) grafts (P=0.043). Acute 2 hour graft patency was 100% for the cross-linked silyl-heparin (6/6) grafts versus 83.3% for control (5/6) grafts. Cross-linked silyl-heparin coated onto carbon-coated ePTFE vascular grafts resulted in improved graft patency, increased in vivo graft thromboresistance, and a significant reduction in intraluminal graft thrombus.

EXAMPLE 16

In the study as described in Example 15, $^{111}$Indium-labeled autologous platelets were injected to study platelet attachment. In an acute 2 hour group, radiolabeled platelets were injected intravenously 10 minutes before aortic and iliac artery unclamping. Circulation was reestablished through both grafts simultaneously and maintained for 120 minutes prior to explanation. In both the 7-day and 30-day groups, dogs were anesthetized and injected with radiolabeled platelets, followed by a 120 minute circulation period. Table 2 depicts $^{111}$Indium radiolabeled platelet deposition, in CPM per cm$^2$ per million platelets injected, mean ±SD, N=5, and where *p=0.029 by paired Student-T test.

TABLE 2

| GROUP | CONTROL GRAFTS | SILYL-HEPARIN CROSS-LINKED GRAFTS |
|---|---|---|
| 2-Hour | 40.1 ± 58.1 | 3.32 ± 2.42 |
| 7-Day | 13.9 ± 22.2 | 21.8 ± 12.1 |
| 30-Day* | 28.4 ± 9.73* | 13.8 ± 7.18* |

EXAMPLE 17

The heparin activity of the cross-linked silyl-heparin coated grafts of Example 15 was determined using a modified anti-thrombin III based thrombin binding assay. The assay utilized a defined concentration of antithrombin III and thrombin in excess. In the assay, antithrombin III binds with heparin. The resulting heparin-antithrombin III complex then bound and inactivated thrombin. Residual thrombin was free to react with the chromogenic substrate S2238 (DiaPharma, West Chester, Ohio), liberating a chromaphore that absorbs at 405 nanometers. Results obtained on absorption of the resulting solution at 405 nanometers were determined by use of a heparin standard curve generated by incubating heparin at various concentrations (range 0.005 to 0.02 IU/mL with antithrombin III and thrombin. An aliquot (20 microliters) of each solution was then assayed as above. The upper limit of the assay was 0.57 IU per $cm^2$ of graft. Intra-assay and inter-assay coefficients of variation were less than 10%. Heparin activity of silyl-heparin grafts was measured before and after explant. Heparin activity was expressed in IU per $cm^2$ of graft. Based on calculations obtained during the coating process, the pre-implant activity of the cross-linked silyl-heparin grafts was estimated to be 2.0 IU per $cm^2$ of graft. After a 2 hour implantation, the activity of the silyl-heparin bonded grafts remained above the upper limit of the heparin assay (0.57 IU per $cm^2$ of graft). After 7 days implanted, the activity decreased to 0.106±0.015 IU per $cm^2$ of graft (5.3% of pre-implant activity). The activity of the silyl-heparin bonded grafts further decreased, after 30 days implanted, to 0.007±0.001 IU per $cm^2$ of graft (0.35% of pre-implant activity).

EXAMPLE 18

Figure 3:
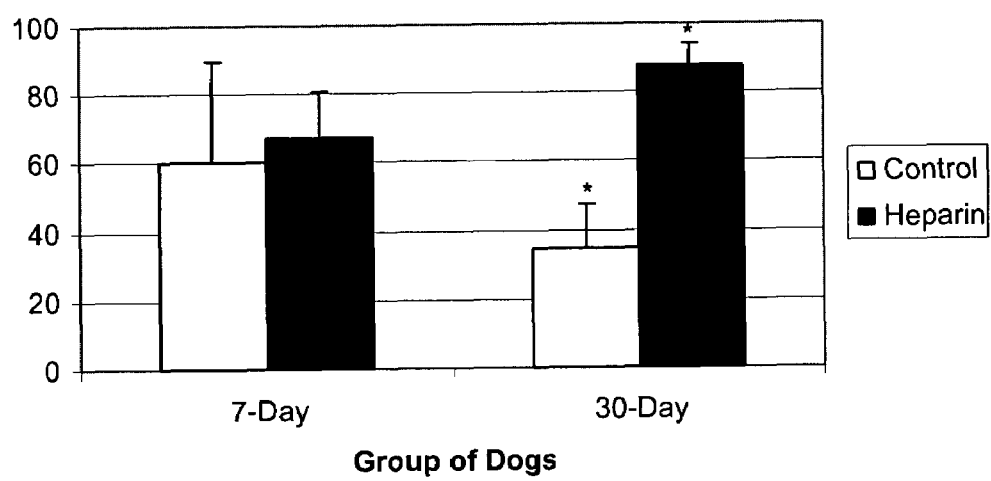
FIG. 3 is a graph of the percent of grafts that are thrombus free in grafts coated with cross-linked silyl-heparin of this invention and control grafts for both chronic 7-day and 30-day groups of dogs, where the Y axis depicts percent of grafts free of thrombus, and where N=5, means are ±SD, and the *p value is 0.0017 as determined by Student-T test.

Histologic analysis was performed on explanted grafts of Example 15 from the 7-day and 30-day groups. The acute (2 hour) group of explanted grafts did not undergo histologic evaluation because microscopic differences observed within a 2 hour implantation were negligible. Analysis was performed on a 2 mm wide, longitudinal strip of graft taken at the time of explanation, fixed in 4% paraformaldehyde and stained with hematoxylin and eosin, subsequent to decay of radioactivity. Photomicrographs were taken of stained graft segments and histologic parameters were determined by computerized planimetry. Histologic parameters measured were graft length, thrombus length, thrombus area, and maximal thrombus height. From these measurements, percent of graft length free of thrombus could be calculated (graft length-thrombus length/graft length×100) as well as average height of thrombus (area of thrombus/thrombus length). The results are shown at FIGS. 2A through 2D. Histologic analysis of grafts revealed a significantly lower amount of intraluminal thrombus on the silyl-heparin bonded grafts compared with control grafts in the 30-day group of animals. This was consistent in all histologic parameters measured. As shown in FIG. 3, the percent of graft free of thrombus was also statistically significantly different in the 30-day group of animals.

EXAMPLE 19

Silyl-heparin was adsorbed onto carbon-coated ePTFE grafts, but without crosslinking. Graft thromboresistance was improved, but retention of the heparin on the grafts was substantially shorter than heparin retained on cross-linked silyl-heparin grafts of Examples 15 and 17.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of forming a cross-linked coating on a medical device, comprising the steps of:
   (a) immersing the medical device in a first solution comprising an organic solvent and a multifunctional crosslinking agent selected from the group consisting of a bis-variant of polyethylene glycol or polyethylene oxide, and
   (b) immersing the medical device in a second solution wherein the second solution comprises an organic solvent and a cross-linkable biomolecule selected from the group consisting of chondroitin sulfate, heparan sulfate and heparin and rendered surface adsorbable by conjugation with a silyl moiety of formula I

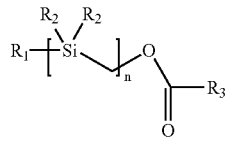

formula I through $R_3$ wherein $R_1$ is an $C_{1-8}$ alkyl or $C_{6-32}$ aryl group, each $R_2$ is independently selected from the group consisting of $C_{1-8}$ alkyl and $C_{6-32}$ aryl, $R_3$ is N or O, and n is a number from 1 to 10.

2. The method of claim 1, wherein prior to immersing the medical device in the first solution or second solution as provided in steps (a) and (b), the medical device is immersed in a wetting solution.

3. The method of claim 1 wherein the first solution does not comprise water and the second solution comprises from about 10 to 80 percent water by volume.

4. A method of forming a thromboresistant coating on a porous surface of a medical device, comprising the ordered steps of:
   (a) providing a medical device with a porous surface;
   (b) immersing the medical device in a first solution comprising an organic solvent and a multifunctional crosslinking agent selected from the group consisting of a bis-variant of polyethylene glycol or polyethylene oxide; and
   (c) immersing the medical device in a second solution wherein the second solution contains a cross-linkable biomolecule selected from the group consisting of chondroitin sulfate, heparan sulfate, and heparin, and heparin rendered surface adsorbable by conjugation with a silyl moiety of formula I

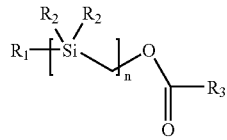

formula I through $R_3$ wherein $R_1$ is an $C_{1-8}$ alkyl or $C_{6-32}$ aryl group, each $R_2$ is independently selected from the group consisting of $C_{1-8}$ alkyl and $C_{6-32}$ aryl $R_3$ is N or O, and n is a number from 1 to 10.

5. The method of claim 4, wherein the medical device comprises expanded polytetrafluoroethylene.

6. The method of claim 1, wherein the wetting solution is an organic solvent.

7. The method of claim 6, wherein the organic solvent is acetone, isopropanol, acetonitrile, methanol, ethanol or any combination thereof.

8. The method of claim 4, wherein the bis-variant of polyethylene glycol or polyethylene oxide is bis-(benzotriazole carbonate) polyethylene glycol.

9. The method of claim 8, wherein the bis-variant of polyethylene glycol or polyethylene oxide is at a concentration between about 0.001 mg/mL and 500 mg/mL.

10. The method of claim 8, wherein the bis-variant of polyethylene glycol or polyethylene oxide is at a concentration between about 0.2 mg/mL and 10 mg/mL.

11. The method of claim 4, wherein the first organic solvent is acetonitrile or acetone, and wherein the first solution does not comprise water.

12. The method of claim 4, wherein the first solution does not comprise water and the second solution comprises from about 10 to 80 percent water by volume.

13. The method of claim 4, wherein the silyl moiety and the cross-linkable biomolecule is at a concentration in the second solution of from about 0.01% to about 10%.

14. The method of claim 4, wherein the silyl moiety and the cross-linkable biomolecule is at a concentration in the second solution of from about 0.25% to about 1.5%.

15. The method of claim 4, wherein the moiety and the cross-linkable biomolecule is benzyl-bis(dimethylsilylmethyl)$_x$-oxycarbamoyl-heparin.

16. The method of claim 4, wherein the second solution further comprises from about 10 to 80 percent water by volume.

17. The method of claim 4, wherein immersing in each step is for between about 5 minutes and two hours.

18. The method of claim 17, wherein immersing the medical device in the first solution is in each step for between about 15 minutes and about one hour.

19. The method of claim 17, wherein immersing the medical device in the second solution is for between about 45 minutes and about 75 minutes.

20. The method of claim 4 further comprising immersing the porous surface in the second solution after immersing the porous surface in the crosslinking solution.

21. The method of claim 4 further comprising wetting the porous surface by immersion in a wetting solution prior to contacting the porous surface with the second solution.

* * * * *